United States Patent
Lin et al.

(10) Patent No.: US 11,006,535 B1
(45) Date of Patent: May 11, 2021

(54) HOUSING CONSTRUCTION FOR SNAP-IN RETENTION

(71) Applicant: Verily Life Sciences LLC, Mountain View, CA (US)

(72) Inventors: Arthur Lin, Fremont, CA (US); Sean Frick, San Francisco, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 0 days.

(21) Appl. No.: 16/785,265

(22) Filed: Feb. 7, 2020

Related U.S. Application Data

(63) Continuation of application No. 16/049,376, filed on Jul. 30, 2018, now Pat. No. 10,624,221.

(60) Provisional application No. 62/546,689, filed on Aug. 17, 2017.

(51) Int. Cl.
| G06F 1/16 | (2006.01) |
| H05K 5/00 | (2006.01) |
| H05K 7/00 | (2006.01) |
| H05K 5/06 | (2006.01) |
| A61B 5/145 | (2006.01) |

(52) U.S. Cl.
CPC ......... *H05K 5/0086* (2013.01); *H05K 5/0004* (2013.01); *H05K 5/069* (2013.01); *A61B 5/14532* (2013.01)

(58) Field of Classification Search
CPC .... H05K 5/069; H05K 5/0004; H05K 5/0086; A61B 5/14532
USPC ............... 361/679.55, 679.56, 679.21–679.3
See application file for complete search history.

(56) References Cited

U.S. PATENT DOCUMENTS

| 7,946,984 | B2* | 5/2011 | Brister | A61B 17/3468 600/365 |
| 8,792,955 | B2* | 7/2014 | Brister | A61B 5/0031 600/345 |
| 9,179,561 | B2* | 11/2015 | Saila | H05K 5/02 |
| 9,669,157 | B2* | 6/2017 | Yodfat | A61M 5/1723 |
| 10,120,409 | B2* | 11/2018 | Osborne | B23K 20/2275 |
| 2010/0110274 | A1* | 5/2010 | Reynolds | G06Q 20/105 348/360 |
| 2010/0155490 | A1* | 6/2010 | Halbur | G06Q 20/349 235/487 |
| 2012/0277667 | A1* | 11/2012 | Yodat | A61B 5/1451 604/65 |
| 2014/0194818 | A1* | 7/2014 | Yodfat | A61M 5/31576 604/151 |
| 2014/0266760 | A1* | 9/2014 | Burke, Jr. | G06F 19/3462 340/687 |
| 2016/0043357 | A1* | 2/2016 | Aida | H01M 2/1066 429/7 |
| 2016/0058380 | A1* | 3/2016 | Lee | A61B 5/68335 600/365 |

OTHER PUBLICATIONS https://www.youtube.com/watch?v=C0PeoDgs4hg;, Aug. 9, 2011.

* cited by examiner

*Primary Examiner* — Anthony M Haughton
(74) *Attorney, Agent, or Firm* — Perkins Coie LLP

(57) ABSTRACT

Introduced here is an attachable unit that connects to a base unit through a snap-fitting mechanism. The attachable unit can include a top housing structure and a bottom housing structure that are ultrasonically welded together. The top housing structure can include the toe portion that is integral with remaining portions of the top housing structure, where the toe portion is configured to provide the snap-fit with the base unit.

20 Claims, 5 Drawing Sheets

HOUSING CONSTRUCTION FOR SNAP-IN RETENTION

CROSS-REFERENCE TO RELATED APPLICATIONS

This application is a continuation of U.S. patent application Ser. No. 16/049,376, filed Jul. 30, 2018, issued as U.S. Pat. No. 10,624,221 on Apr. 14, 2020, which claims benefit of U. S. Provisional Application Ser. No. 62/546,689, filed Aug. 17, 2017, which are incorporated by reference herein in their entirety.

TECHNICAL FIELD

Various embodiments concern techniques for a housing constructions for snap-in retention for a device.

BACKGROUND

Technological advances (e.g., improvements in processors, wireless communication, and packaging materials, in terms of their processing power, power consumption, and size) allow for new perspectives, paradigms, and possibilities. One such example is the development of wearable devices, where devices are worn on the body of the users rather than being separately carried and tracked by users. Further, by being on the person of the users, the wearable devices can provide new features and advantages previously unavailable to carried devices.

However, along with the new possibilities come various new challenges. For example, in integrating with users' daily lives and routines, the wearable devices can be physically stressed in ways that are foreign to other carried devices. Further, wearable devices can encounter unique size and shape limitations associated with users' comfort and mobility, meanwhile being asked to provide ever increasing and more complicated features without increasing the physical size or the cost.

BRIEF DESCRIPTION OF THE DRAWINGS

Various features and characteristics of the present disclosure will become more apparent to those skilled in the art from a study of the Detailed Description in conjunction with the drawings. Embodiments of the present disclosure are illustrated by way of example and not limitation in the drawings, in which like references indicate similar elements.

Figure 1:
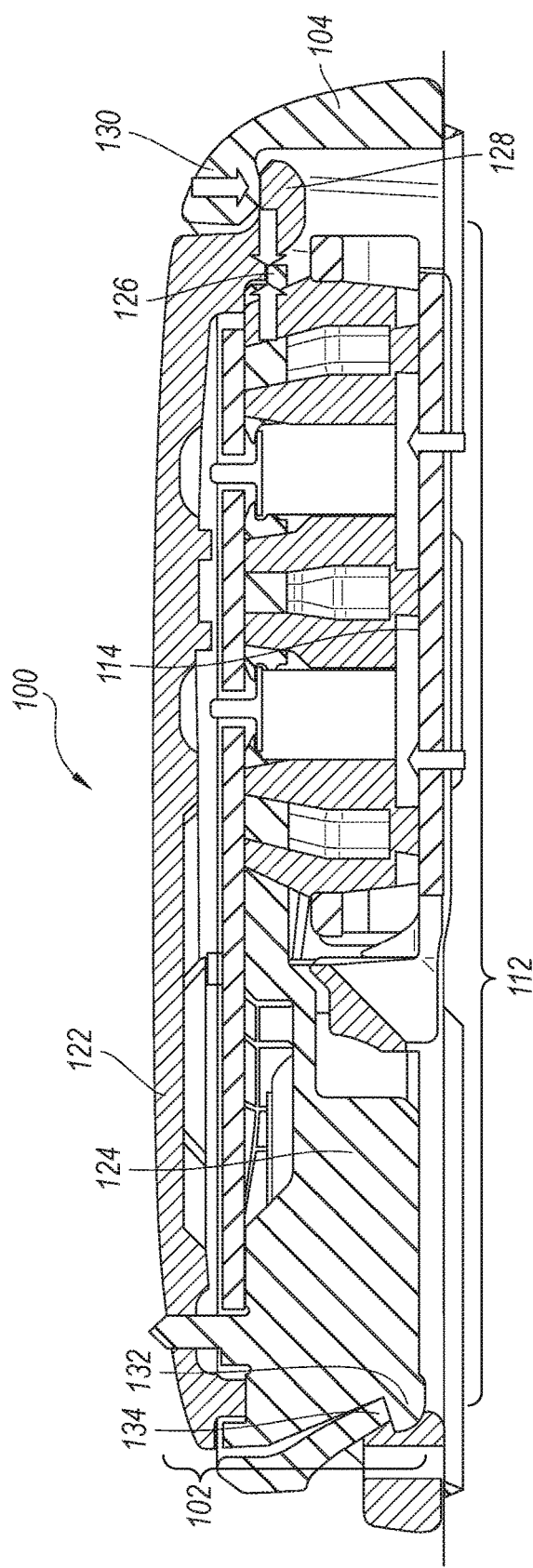
FIG. 1 illustrates a cross-sectional view of an electronic device according to some embodiments.

The drawings depict various embodiments for the purpose of illustration only. Those skilled in the art will recognize that alternative embodiments may be employed without departing from the principles of the disclosed techniques. Accordingly, while specific embodiments are shown in the drawings, the disclosed techniques are amenable to various modifications.

DETAILED DESCRIPTION

Introduced here are techniques for implementing a device (e.g., a wearable device), a system including the device, a method of operation or manufacture of the device/system, etc., that can be configured to provide a snap-fit between multiple units without stressing attachment joints within one or more of the multiple units. The snap-fit can be based on a toe portion of an attachable unit fitting against a base unit. The toe portion can be integral with a remainder of a top housing structure.

The top housing structure can be attached to the bottom housing structure to form the attachable unit. In some embodiments, the top and bottom housing structures can be attached through an ultrasonic welding process. The top housing structure, the bottom housing structure, or a combination thereof can include one or more energy directors (structures included in or integral with welded structures and configured to direct and focus the ultrasonic energy at an apex thereof). When the ultrasonic energy is applied during the welding process, the energy can be focused at the energy directors resulting in rapid increase in thermal energy. As a result, the energy directors or portions thereof can melt and flow across the joint interface to form welds.

The top housing structure can further include one or more support directors (e.g., energy directors integral with or near the integral toe portion with a configuration different from other or primary energy directors). The support directors can be configured (e.g., such as using shapes, locations, corresponding edges or depressions in the bottom housing structure, or a combination thereof) to help alignment of the top housing structure and the bottom housing structure during an alignment stage of manufacturing (for the welding or the final step thereof). The support directors can be further configured (e.g., such as using a cross-sectional shape or an angle at the apex) to function as non-primary energy directors that melt after the primary energy directors for the ultrasonic welding process.

For example, the support directors can fit into corresponding support receptors (e.g., cavities or depressions) in the bottom housing structure to provide a mechanical fit and/or alignment between the two structures during the alignment stage of manufacturing. The support directors can be shaped to melt at some time after the primary directors during a welding stage of manufacturing, thereby providing the mechanical fit and/or alignment during the ultrasonic welding stage. Further, the support directors can also melt toward the latter part of the welding stage and provide further adherence between the top housing structure and the bottom housing structure after the ultrasonic welding process.

The primary energy directors, the support director, the support receptor, the integral toe portion, or any combination thereof can be configured (e.g., based on physical design parameters, such as relative location, alignment, size, shape, etc., of various portions and components) to direct any external and/or internal forces to compress the welded joints during use or deployment of the attachable unit. Accordingly, the configurations discussed in the various embodiments below can provide increased robustness and structural integrity by compressing the ultrasonic weld joint and avoiding any tensile stress that would damage the weld joint.

Although some embodiments may be described in the context of wearable devices, the disclosed techniques are generally implementation-agnostic. That is, various configurations discussed below can be utilized regardless of usage or application of the overall structure or device (e.g., for a carried device or a static/non-mobile device).

Terminology

References in this description to "an embodiment" or "one embodiment" means that the particular feature, function, structure, or characteristic being described is included in at least one embodiment. Occurrences of such phrases do not necessarily refer to the same embodiment, nor are they necessarily referring to alternative embodiments that are mutually exclusive of one another.

Unless the context clearly requires otherwise, the words "comprise" and "comprising" are to be construed in an inclusive sense rather than an exclusive or exhaustive sense (i.e., in the sense of "including but not limited to"). The terms "connected," "coupled," or any variant thereof is intended to include any connection or coupling, either direct or indirect, between two or more elements. The coupling/connection can be physical, logical, or a combination thereof. For example, two devices may be communicatively coupled to one another despite not sharing a physical connection.

The term "integral" is intended to describe a physical continuum between portions of one continuous object or structure. Portions that are integral to an object or a structure can be formed (e.g., by molding or by removing from a starting structure) together with the object or the structure, and can consist of same material as the remaining portions of the object or the structure. A portion that is integral with another portion is different from two objects that are separately formed and subsequently joined or attached (e.g., using adhesives, using mechanical interlocking forces, or by welding or melting components together).

When used in reference to a list of multiple items, the word "or" is intended to cover all of the following interpretations: any of the items in the list, all of the items in the list, and any combination of items in the list.

Technology Overview

FIG. 1 illustrates a cross-sectional view of an electronic device 100 according to some embodiments. The electronic device 100 can include a wearable device (e.g., a wearable health monitor, such as a glucose monitor). The electronic device 100 can include an attachable unit 102 and a base unit 104. As shown in FIG. 1, the base unit 104 can be located on the bottom and the attachable unit 102 can be located above the base unit 104 and/or within a cavity 112 of the base unit 104. In some embodiments, the base unit 104 can fit within a cavity of the attachable unit 102.

In some embodiments, the base unit 104 can include a structure for housing the attachable unit 102. In some embodiments, the base unit 104 can include a structure for interfacing with or contacting the body or person of a user. The base unit 104 can include an interfacing element 114 (e.g., a sealing element) that can be compressed. For example, the base unit 104 can include an elastomeric sealing element to prevent ingress of moisture to sensitive areas of the device.

In some embodiments, the attachable unit 102 can include electronic components or circuits, such as a processor, a memory, an analog circuit component, a filter, a sensor, a communication device, etc. For example, the attachable unit 102 can include a sensor, a processor, a memory, and a transmitter for measuring, processing, and communicating information (e.g., measured glucose levels and/or status of the wearable device) to another device.

The attachable unit 102 can include a top housing structure 122 and a bottom housing structure 124 encasing the electrical components. The top housing structure 122 and the bottom housing structure 124 can be joined or attached together using a variety of methods. For illustrative purposes, the top housing structure 122 and the bottom housing structure 124 are described below as being made from plastic material and attached through an ultrasonic welding process (e.g., using locally-applied ultrasonic vibrations to create solid-state weld). However, it is understood that the structures can be made from different materials and attached using other mechanisms, such as using an adhesive, interlocking structural shapes, sintering or other welding mechanisms (e.g., arc welding or laser welding), etc.

Based on the attachment mechanism, the attachable unit 102 can include one or more attachment locations 126 (e.g., weld spots) where the top housing structure 122 is attached to the bottom housing structure 124. For example, the weld spots can correspond to locations of one or more energy directors on the top housing structure 122, the bottom housing structure 124, or both.

The ultrasonically welded attachable unit 102 can be attached to the base unit 104 using a different mechanism, such that the attachable unit 102 can be removed from or physically reconfigured relative to the base unit 104. For example, the attachable unit 102 and the base unit 104 can be attached to each other using shapes or portions therein that interlock with each other, such as for providing a snap-fit. The attachable unit 102 can include a toe portion 128 that can interlock with a fitting tab 130 integral with the base unit 104, a protrusion 132 that can interlock with a second tab 134, etc. to provide a cantilever type snap-fit between the attachable unit 102 and the base unit 104.

The protrusion 132 can be located horizontally opposite the toe portion 128, such as on opposite sides of a middle portion of the attachable unit 102. In some embodiments, the protrusion 132 can be attached to and/or integral with the bottom housing structure 124. In some embodiments, the protrusion 132 can be located below the tow portion 128. The protrusion 132 can be configured to directly contact and interlock with the second tab 134 that is located horizontally opposite the fitting tab 130, such as on opposing sides of the base unit 104 and the cavity 112. In some embodiments, the second tab 134 can extend downward and/or below the fitting tab 130.

The toe portion 128 can extend away (e.g., along a vertical and/or a horizontal direction) from a peripheral edge of the attachable unit 102. As illustrated in FIG. 1, the toe portion 128 can extend away from a center portion of the attachable unit 102 for a snap-fit configuration that includes the toe portion 128 encompassed within peripheral portions of the base unit 104. The toe portion 128 can include a contacting surface, which can be located below a top surface of the attachable unit 102, that is configured to contact a corresponding surface located on the bottom of the fitting tab 130 that is integral with the base unit 104. In some embodiments, the toe portion 128 can extend toward the center portion for a different snap-fit configuration that includes the peripheral portions of the top unit or the toe portion 128 thereof encompassing the fitting tab 130 and/or the peripheral portions of the base unit 104.

When the attachable unit 102 is snapped into the base unit 104, internal components or configuration (e.g., the elastomeric sealing element) can provide directional forces that create tension at the interlock joint and/or throughout the various units. For example, when inserted and locked into the base unit 104, the top attachable unit 102 can compress the elastomeric sealing element within the base unit 104. Accordingly, the elastomeric sealing element can press upward against the attachable unit 102 after attachment.

As such, the configuration for the toe portion 128, the weld joints, or a combination thereof can account for the directional forces to provide increased structural integrity. For example, the toe portion 128 can be formed integral with the top housing structure 122 instead of the bottom housing structure 124 and the energy directors (e.g., the corresponding weld joint) can be located near (e.g., within a threshold distance from) the toe portion 128. With top housing structure 122 including the toe portion 128 as an integral portion therein and the weld joints located near the toe portion 128, the configuration can direct the upward forces from the elastomeric sealing element to compress the weld joint. The compressing forces can reinforce the weld joint in the attachable unit 102. In comparison, including the toe portion 128 in the bottom housing structure 124 can result in a loading situation that imparts tensile stress to the weld joints. Over time, the tensile stress can cause a creep or stress crack failure where the top housing structure 122 is peeled open and separated from the bottom housing structure 124.

In some embodiments, the base unit 104 can be more rigid than the attachable unit 102 (e.g., as a result of difference in structural material, structural designs, other attachments, or a combination thereof). For example, the attachable unit 102 or a portion therein (e.g., the top housing structure 122) can be made of plastic material that is more flexible, has a thinner cross section, or a combination thereof than the base structure. In some embodiments, the bottom housing structure 124 can similarly (e.g., as a result of difference in structural material, structural designs, other attachments, or a combination thereof) be more rigid than the top housing structure 122. Due to the difference in rigidity and the upward forces (e.g., as illustrated with vertical solid arrows) from the elastomeric sealing element, the fitting tab 130 can apply a downward force on and/or bend the integral toe portion 128 when the attachable unit 102 attaches to the base unit 104. Correspondingly, the integral toe portion 128 can transfer or direct the various forces to compress (e.g., as illustrated with horizontal solid arrows) the weld joints that attach the top and bottom housing structures. One or more of the weld joints can be located (e.g., vertically and/or horizontally) within a threshold distance (e.g., less than ¼ of a corresponding dimension of the top housing structure 122) from the integral toe portion 128.

The energy directors (e.g., the primary and/or the support directors) can be configured (e.g., in shape, quantity, location, or a combination thereof) according to the difference in rigidity. The energy directors can be configured to control rigidity throughout the attachable unit 102, such as by controlling a distance between weld joints. For example, the energy directors can be configured to shorten bendable portions of the attachable unit 102, the top housing structure 122, or a combination thereof and increase rigidity in the attachable unit 102, the top housing structure 122, or a combination thereof.

In some embodiments, the attachable unit 102 can be manufactured without an encapsulation. Based on the configuration of the integral toe portion 128, the energy directors (e.g., the primary and/or the support directors), the top housing structure 122 (e.g., a relative flexibility and shape in relation to the bottom housing structure 124), or a combination thereof the attachable unit 102 can hermetically seal the internal components therein without using separate encapsulation or adhesive material.

Figure 2:
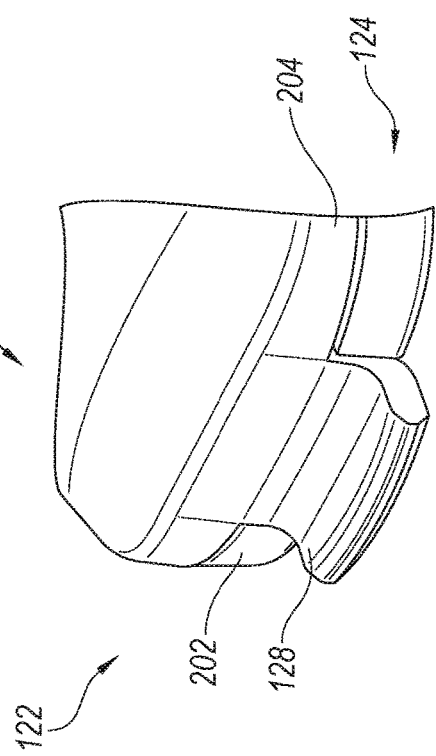
FIG. 2 illustrates a perspective view of a portion of an upper housing structure for the electronic device of FIG. 1 with a toe integral with the portion according to some embodiments.

FIG. 2 illustrates a detailed view of a portion of an upper housing structure for the electronic device 100 of FIG. 1 with a toe integral with the portion according to some embodiments. As mentioned above, the attachable unit 102 can include the top housing structure 122 and the bottom housing structure 124 ultrasonically welded together. The top housing structure 122, the bottom housing structure 124, or a combination thereof can be made of plastic material.

When welded together, the top housing structure 122 and the bottom housing structure 124 can form an enclosure that contains the various components (e.g., electronic components, circuits, etc.). In some embodiments, a bottom-structure peripheral surface 202 can be aligned with a top-structure peripheral surface 204 along a vertical line/plane. In some embodiments, the bottom-structure peripheral surface 202 can be between the top-structure peripheral surface 204 and a center portion of the top housing structure 122 and/or the bottom housing structure 124.

The top housing structure 122 can include the toe portion 128 that is integral with remaining portions (e.g., cover portion) of the top housing structure 122. The toe portion 128 can be located below the top surface or the cover portion of the top housing structure 122. The toe portion 128 can further be horizontally adjacent to the bottom housing structure 124, such as a peripheral edge/surface thereof. An interior surface (not shown) of the toe portion 128 can directly contact a peripheral surface of the bottom housing structure 124.

Further, the toe portion 128 can include the top surface including a transitional section that extends down and/or away from a peripheral surface of the cover portion. The transitional section can form a surface with concave shape, such as for an indent or a depression. The transitional section can be integral with the contacting surface that extends horizontally away from the bottom housing structure 124.

Figure 3:
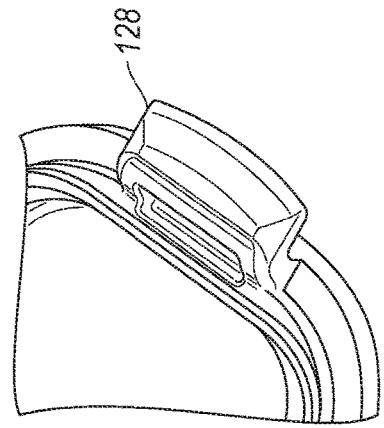
FIG. 3 illustrates a bottom view of a portion of the upper housing structure according to some embodiments.

FIG. 3 illustrates a bottom view of a portion of the upper housing structure according to some embodiments. The top housing structure 122 can include a slot, a tab or an insert, a lip or a wall, or a combination thereof integral with a bottom surface and/or the interior surface of the toe portion 128. The top housing structure 122 can further include energy directors, indents or extrusions, vertical or angled surfaces, or a combination thereof configured to contact the bottom housing structure 124, and form a seal with and/or attach to the bottom housing structure 124.

Figure 4:
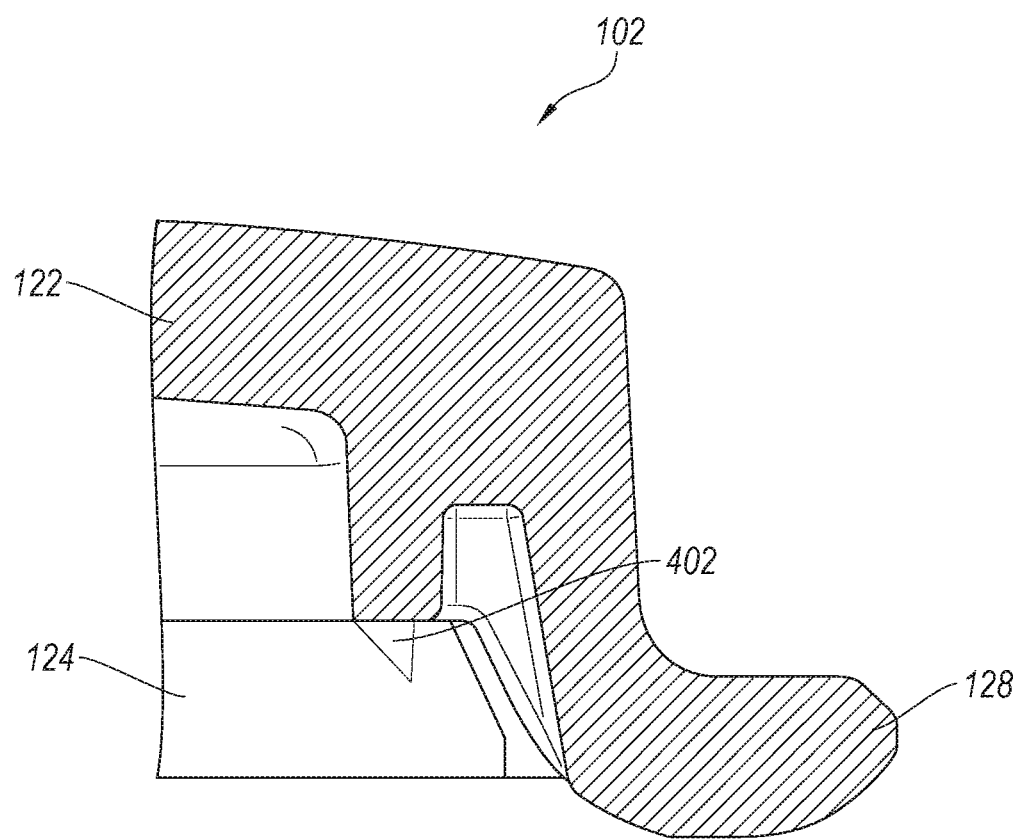
FIG. 4 illustrates a cross-sectional view of a portion of the upper housing structure for the electronic device of FIG. 1 with a toe integral with the portion according to some embodiments.

FIG. 4 illustrates a cross-sectional view of a portion of the upper housing structure for the electronic device 100 of FIG. 1 with a toe integral with the portion according to some embodiment. The cross-sectional view illustrates details of attachment or joint between the top housing structure 122 and the bottom housing structure 124 of the attachable unit 102.

In facilitating the attachment or joint between the structures, the upper housing structure can include one or more energy directors 402 inserted below a top surface of the bottom housing structure 124. The energy directors 402 can have a tapered shape for the cross-section. For example, the cross-sectional view of the support director 402 can have an inverted peak or triangular cross-sectional shape.

The energy directors 402 can be used to align and/or mechanically connect the top housing structure 122 and the bottom housing structure 124 during the ultrasonic welding process. For example, the energy directors 402 can be inserted into depressions or receptors in the bottom housing structure 124 before or for the ultrasonic welding process. The energy directors 402 can be configured to melt at some point during the ultrasonic welding process, such as by having a size, shape, configuration, etc. configured to focus the ultrasonic energy and raise the temperature at the focused location. After cooling, the melted material can solidify and form an attachment or joint between the top housing structure 122 and the bottom housing structure 124.

Figure 5A:
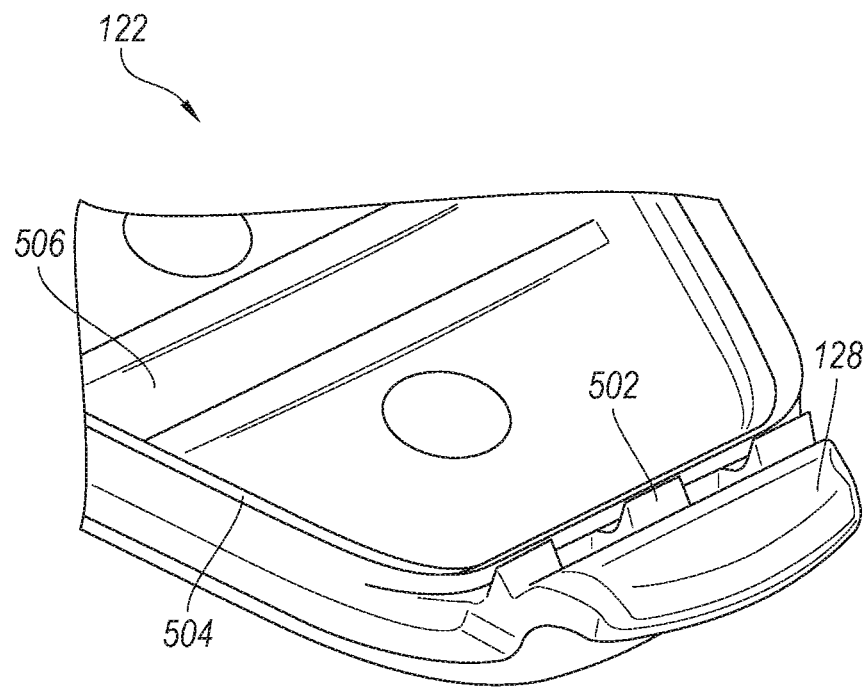
FIGS. 5A-B illustrate further bottom views of a portion of the top housing according to some embodiments.
Figure 5B:
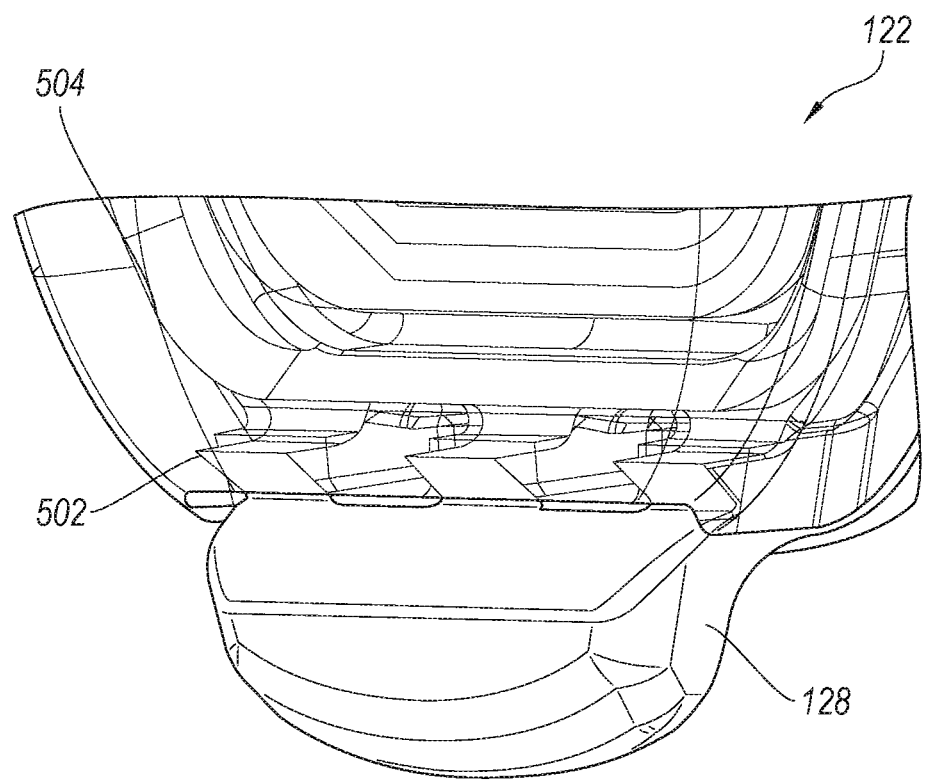

FIGS. 5A-B illustrate further bottom views of a portion of the top housing according to some embodiments. The top housing structure 122 can include multiple support directors 502 (e.g., a set of the energy directors 402 of FIG. 4), which can be integral with and/or extend from the interior surface of the toe portion 128, the bottom surface of the cover portion, a column extending from the bottom surface, etc. The support directors 502 can be located between the interior surface and a sealing protrusion or a primary energy director 504 (e.g., one of the energy directors 402).

The support director 502 can be used to align and/or mechanically connect the top housing structure 122 and the bottom housing structure 124 during the ultrasonic welding process. For example, the support director 502 can be inserted into depressions or receptors in the bottom housing structure 124 before or for the ultrasonic welding process. The support director 502 can be configured to melt at some point after other energy directors (e.g., after primary energy directors 504 based on modulation of the ultrasonics) during the ultrasonic welding process, such as by having a size smaller than the other energy directors and/or by having a specific shape or different relative height (e.g., the height of the directors can be such that primary is taller for melting first, then the secondary shorter for contacting a little later and melting after).

In some embodiments, the support director 502 can include one or more protrusions extending away (e.g. vertically) from a bottom surface 506 of the top housing structure 122. The one or more protrusions can be separated by gaps. In some embodiments, the one or more protrusions can be attached to or integral with an inner surface/portion of the toe portion 128. In some embodiments, the one or more protrusions can include a first (e.g., vertical) surface and a second (e.g., angled or slanted) surface forming an apex point/edge. The first surface can be adjacent to the primary energy director 504 and the second surface can be adjacent to the toe portion 128.

In some embodiments, the primary energy director 504 can extend away (e.g., vertically) from the bottom surface 506. In some embodiments, the primary energy director 504 can be a continuous wall located on perimeter portions of the top housing structure 122. The primary director 504 can include a first (e.g., vertical) surface and a second (e.g., angled or slanted) surface forming an apex edge. The first surface can be adjacent to the support director 502 and the second surface can face the inner/center portion of the top housing structure 122.

Figure 6A:
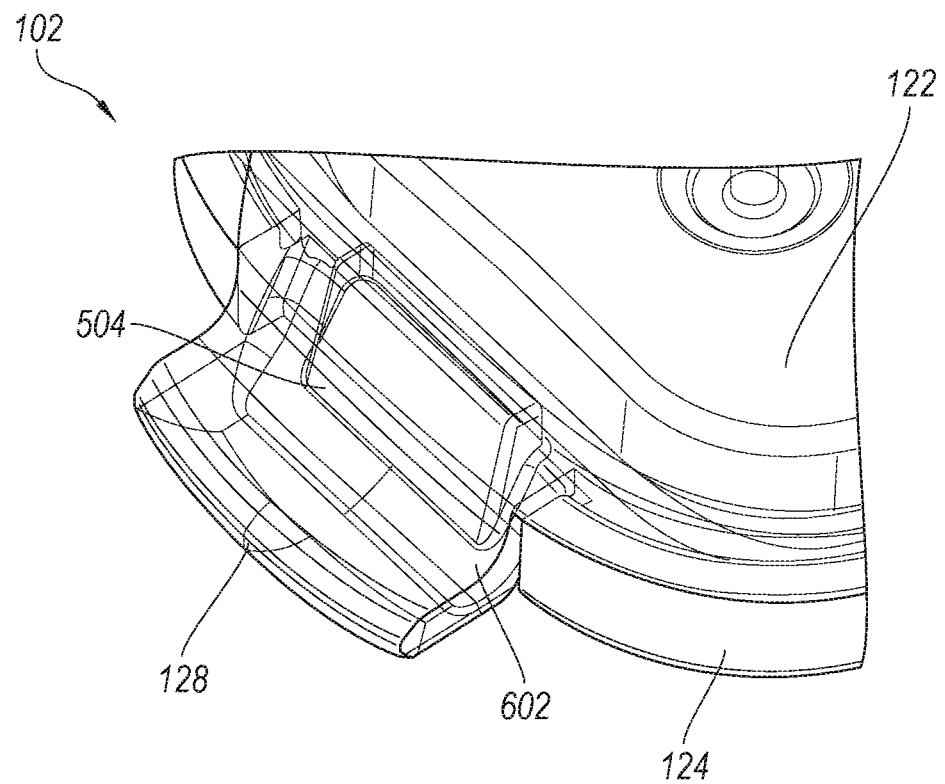
FIGS. 6A-B illustrate a detailed view and a cross sectional view of the top housing joined with a bottom housing according to some embodiments.
Figure 6B:
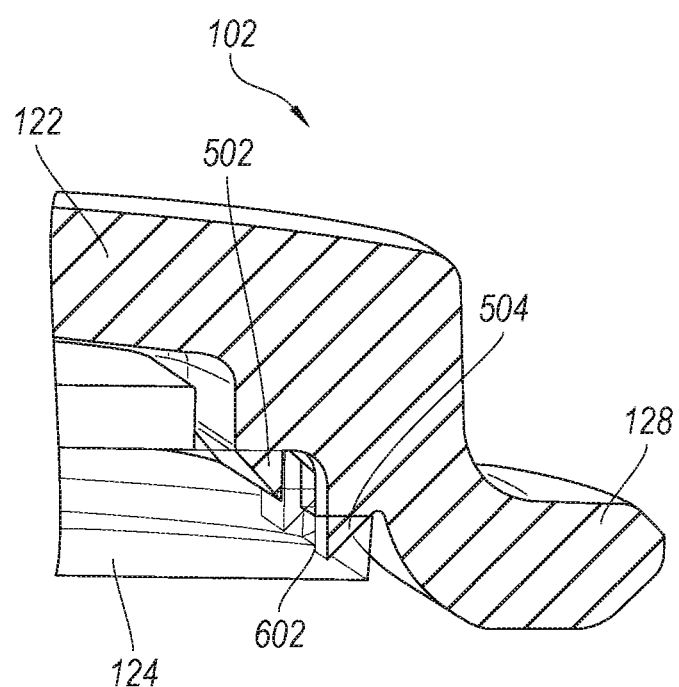

FIGS. 6A-B illustrate a detailed view and a cross sectional view of the top housing joined with a bottom housing according to some embodiments. The bottom housing structure 124 can include one or more support receptors 602 (e.g., holes, depressions, or cavities in a top surface of the bottom housing structure 124) that correspond to the support directors 502. The support directors 502 and the support receptors 602 can be aligned and correspond to the attachment locations 126 (e.g., locations of the weld spots) for the attachable unit 102. The support directors 502 can be inserted into the support receptors 602 for the ultrasonic welding process.

The support director 502 can be located near (e.g., within a threshold distance along a horizontal direction) the toe portion 128. After the welding process, the arrangement and/or the relative locations of the toe portion 128 and the support director 502 can strengthen the connection between the top housing structure 122 and the bottom housing structure 124. For example, the toe portion 128 and the support director 502 can minimize deflection between the toe portion 128 in the upper housing structure and the lower housing structure.

In some embodiments, the support directors 502 can be located between a further set of energy directors (e.g., primary energy directors 504) and the integral toe portion 128, such as along a horizontal direction and/or a vertical direction. One or more of the support directors 502 can be located below one or more of the primary energy directors 504. As illustrated in FIG. 6B, the support directors 502 can be located below the further set of directors and outside (e.g., relative to a center portion of the structure) of the further director. The support directors 502 can be further located above or coplanar with a center portion of the integral toe portion 128 and inside of the integral toe portion 128. The bottom housing structure 124 can include a step or a sloped portion at a periphery portion adjacent to the integral toe portion 128, where the step or sloped portion corresponds to arrangement of the further set of directors and the support directors 502.

Further, the support directors 502 and the further directors can have opposing shapes. The support director 502 and/or the further directors can have a tapered shape for the cross-section, such as for an inverted peak or triangular cross-sectional shape. For example, the support directors 502 can each have a vertical surface forming an apex with a slanted surface extending down and toward the center portion. The further directors can also have a vertical surface that is opposite to or facing the vertical surface of the support directors 502, that also form an apex with a slanted surface extending down and away from the center portion.

The relative locations and/or shapes of the further directors, the support directors 502, and the integral toe portion 128 can direct the above discussed forces to compress the weld joints and increase the strength and integrity of the weld spots. The location of the support directors 502 relative to the further directors and the integral toe portion 128 can further shorten a distance between the integral toe portion 128 to the nearest weld spot, thereby reducing a length of bendable portions near the integral toe portion 128 and further increasing the strength and integrity of the weld spots.

Manufacturing Overview

Figure 7:
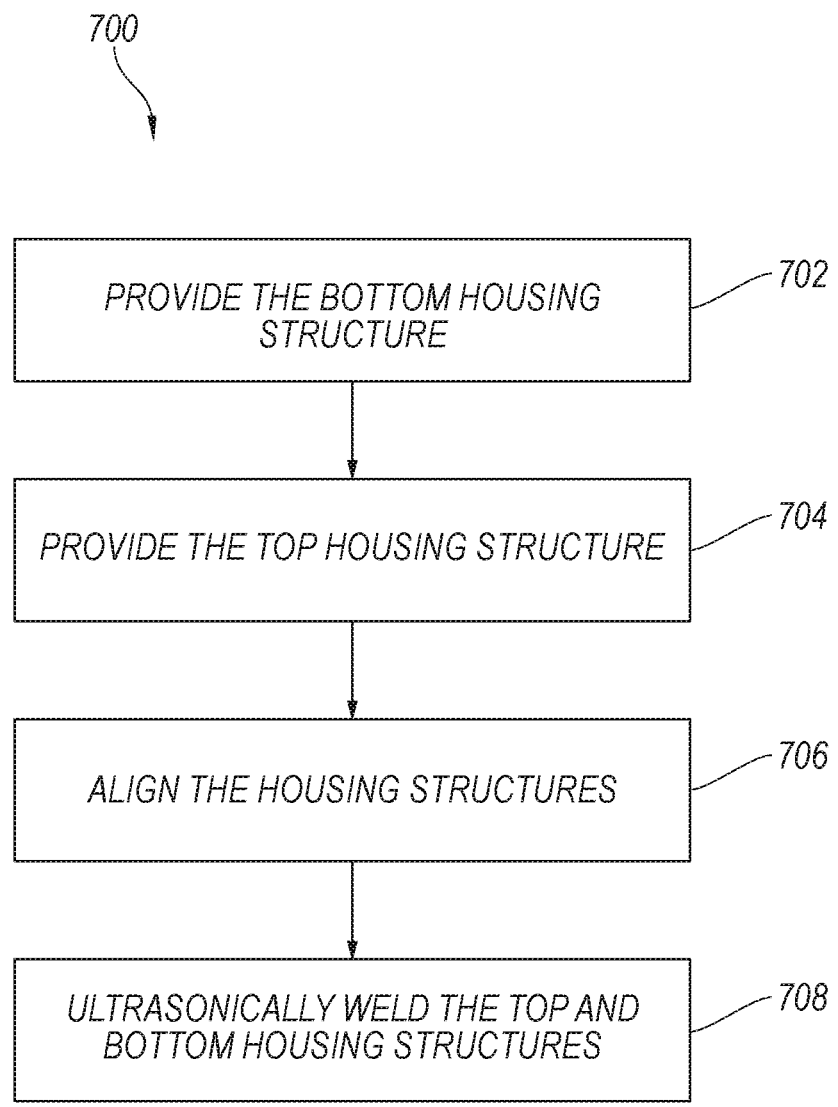
FIG. 7 illustrates an example method of manufacturing the electronic device according to some embodiments.

FIG. 7 illustrates an example method 700 of manufacturing the electronic device 100 of FIG. 1 according to some embodiments. The method 700 can manufacture the attachable unit 102 of FIG. 1 based on providing the bottom housing structure 124 of FIG. 1 (as illustrated at block 702), providing the top housing structure 122 of FIG. 1 (as illustrated at block 704), align the two housing structures (as illustrated at block 706), and ultrasonically welding the two housing structures together (as illustrated at block 708). The method 700 can further manufacture the base unit 104 of FIG. 1 (not shown), attach the attachable unit 102 to the base unit 104 (not shown) or a combination thereof.

In some embodiments, providing the top and/or bottom housing structures can include forming or manufacturing the structure, such as by shaping a plastic material. For example, the housing structures can be shaped using techniques such as molding or casting (e.g., based on hardening liquid or pliable material such as plastic inside shaped molds), forming or machining (e.g., based on cutting or removing portions of raw material), deposition or three-dimensional printing, joining or attaching, or a combination thereof. The housing structures can be shaped to have the portions (e.g., the integral toe portion 128 of FIG. 1, the energy directors, the fitting tab 130 of FIG. 1, or a combination thereof) according to a specific configuration (e.g., for shapes, sizes, locations, or a combination thereof). Further, the housing structures can be shaped or formed to provide specified rigidity (e.g., based on the raw material used for the forming process, based on varying thickness or density of material, or a combination thereof).

In some embodiments, providing the top and/or bottom housing structures can include placing the structure on a mount for movement during subsequent stages of the manufacturing process. The structures can be placed and/or attached to specific locations or mounts. For example, the bottom housing structure 124 can be placed on and/or attached to a specific location of a nest or an anvil portion of an ultrasonic welding apparatus. The top housing structure 122 can be attached to a press portion of the ultrasonic welding apparatus. The press portion can be located above the nest or anvil portion.

In some embodiments, aligning the housing structures can include arranging the structures in physical space to overlap each other (e.g., aligning the structures such that corresponding portions on each of the structures contact one plane or line, such as having the support director is directly over the support receptor 602 of FIG. 6). For example, the housing structures can be aligned based on placing and/or attaching the housing structures at a location configured to align the structures. Also for example, the housing structures can be aligned based on moving or displacing the press portion or a mount thereon that is attached to the top housing structure 122.

Aligning the housing structures can further include moving one or more of the housing portions such that the housing structures contact each other at one or more points. For example, the housing structures can be placed on or attached to the press portion that is above the anvil portion, where the press portion is configured to move down along a vertical line. The alignment step can include placing the housing structures according to a location and an orientation on horizontal planes, and then moving the press portion down until the housing structures directly contact each other (e.g., with the energy directors contacting the corresponding locations on the complementary structure).

In some embodiments, ultrasonically welding the structures can include applying ultrasonic energy to the top housing section, the bottom housing section, one or more portions therein, or a combination thereof. For example, the ultrasonic welding apparatus can generate and apply ultrasonic energy to one or more locations on the top housing section, the bottom housing section, or both. Based on the physical configuration of the structures and the energy directors therein, the ultrasonic energy can be focused at a location (e.g., an apex) on each of the energy directors. The focus in energy can increase the temperature at the corresponding location and melt the energy directors or portions therein. During the application of ultrasonic energy, the support directors 502 of FIG. 5 can melt after the primary energy directors 504 of FIG. 5. After a duration, the ultrasonic welding apparatus can stop applying the energy. Temperatures at the weld spots can be reduced below the melting point of the material based on removal of the energy, change in shape of the energy directors based on melting (i.e., thereby no longer focusing the applied energy), or a combination thereof. The melted material can harden as the temperature decreases, thereby forming a weld that attaches the two structures to each other.

Remarks

The foregoing description of various embodiments of the claimed subject matter has been provided for the purposes of illustration and description. It is not intended to be exhaustive or to limit the claimed subject matter to the precise forms disclosed. Many modifications and variations will be apparent to one skilled in the art. Embodiments were chosen and described in order to best describe the principles of the invention and its practical applications, thereby enabling those skilled in the relevant art to understand the claimed subject matter, the various embodiments, and the various modifications that are suited to the particular uses contemplated.

Although the Detailed Description describes certain embodiments and the best mode contemplated, the presented techniques can be practiced in many ways no matter how detailed the Detailed Description appears. Embodiments may vary considerably in their implementation details, while still being encompassed by the specification. Particular terminology used when describing certain features or aspects of various embodiments should not be taken to imply that the terminology is being redefined herein to be restricted to any specific characteristics, features, or aspects of the presented techniques with which that terminology is associated. In general, the terms used in the following claims should not be construed to limit the presented techniques to the specific embodiments disclosed in the specification, unless those terms are explicitly defined herein. Accordingly, the actual scope of the presented techniques encompasses not only the disclosed embodiments, but also all equivalent ways of practicing or implementing the embodiments.

The language used in the specification has been principally selected for readability and instructional purposes. It may not have been selected to delineate or circumscribe the subject matter. It is therefore intended that the scope of the presented techniques be limited not by this Detailed Description, but rather by any claims that issue on an application based hereon. Accordingly, the disclosure of various embodiments is intended to be illustrative, but not limiting, of the scope of the presented techniques as set forth in the following examples.

We claim:

1. An electronic device comprising:
   a base unit including:
     a top surface forming a cavity with a peripheral edge, and
     a fitting tab integral with the peripheral edge and located above the top surface; and
   an attachable unit configured to fit inside the cavity and connect to the base unit, wherein the attachable unit includes:
     a bottom housing structure adapted to fit over the top surface of the base unit when the attachable unit is fitted inside the cavity, and
     a top housing structure ultrasonically welded to the bottom housing structure, wherein the top housing structure (1) includes an integral toe portion configured to interlock with the fitting tab when the attachable unit is inside the cavity and (2) is adapted to fit over the bottom housing structure when the attachable unit is fitted inside the cavity.

2. The electronic device of claim 1, wherein:
the fitting tab includes an arm portion and a locking portion, wherein the arm portion is integral with the top surface, extends away from the top surface, and is integral with the locking portion opposite to the top surface; and
the integral toe portion is located below and directly contacting the locking portion interlock with the fitting tab when the attachable unit is inside the cavity.

3. The electronic device of claim 1, wherein the top housing structure includes a support director integral with a bottom surface thereof and located near the toe portion and between the toe portion and a center portion, wherein the support director is an energy director for an ultrasonic welding process that attaches the top housing structure and the bottom housing structure.

4. The electronic device of claim 3, wherein the top housing structure includes a primary director configured to melt before the support director during the ultrasonic welding process.

5. The electronic device of claim 4, wherein the support director is located between the primary director and the integral toe portion, located below the primary director, or a combination thereof.

6. The electronic device of claim 4, wherein the support directors are configured to provide a mechanical fit and/or alignment between the bottom housing structure and the top housing structure during an ultrasonic welding stage.

7. The electronic device of claim 1, wherein the attachable unit includes:
one or more ultrasonic weld spots attaching the bottom housing structure and the top housing structure;
the integral toe portion of the top housing structure configured to direct forces to compress the ultrasonic weld spots when the attachable unit is inside the cavity.

8. The electronic device of claim 7, wherein the integral toe portion is configured to receive a downward force from the fitting tab and direct the downward force to compress the weld spots that are located within a threshold distance from the integral toe portion.

9. The electronic device of claim 1, wherein:
the top surface includes:
a second peripheral edge forming the cavity and located horizontally opposite the peripheral edge,
a second tab integral with the second peripheral edge and above the top surface; and
the attachable unit includes a protrusion located horizontally opposite the integral toe portion, wherein the protrusion is configured to contact and interlock with the second tab when the attachable unit is inside the cavity.

10. The electronic device of claim 9, wherein:
the second tab extends downward and below the fitting tab;
the protrusion is integral with the bottom housing structure, located below the integral toe portion, and extends horizontally away from a peripheral surface thereof; and
the attachable unit includes one or more ultrasonic weld spots attaching the bottom housing structure and the top housing structure, wherein the one or more ultrasonic weld spots are located between the protrusion and the integral toe portion.

11. An electronic device comprising:
a bottom housing structure; and
a top housing structure ultrasonically welded to the bottom housing structure, wherein the top housing structure includes an integral toe portion for providing a snap-fit with a base unit when the ultrasonically welded combination of the bottom housing structure and the top housing structure is placed within a cavity of the base unit with the bottom housing structure fitting over the cavity and the top housing structure over the bottom housing structure.

12. The electronic device of claim 11, wherein the integral toe portion is configured, through shape and a relative location with respect to a corresponding portion in the base unit, to directly contact and interlock with the corresponding portion when the device is placed within the cavity.

13. The electronic device of claim 11, wherein the top housing structure includes a support director integral with a bottom surface thereof and located near the toe portion and between the toe portion and a center portion, wherein the support director is an energy director for an ultrasonic welding process that attaches the top housing structure and the bottom housing structure.

14. The electronic device of claim 13, wherein the top housing structure includes a primary director configured to melt before the support director during the ultrasonic welding process.

15. The electronic device of claim 14, wherein the support director is located between the primary director and the integral toe portion, located below the primary director, or a combination thereof.

16. The electronic device of claim 11, further comprising:
one or more ultrasonic weld spots attaching the bottom housing structure to the top housing structure;
the integral toe portion of the top housing structure configured to direct forces to compress the ultrasonic weld spots when the attachable unit is inside the cavity.

17. The electronic device of claim 16, wherein the integral toe portion is configured to receive a downward force from the base unit direct the downward force to compress the weld spots that are located within a threshold distance from the integral toe portion.

18. The electronic device of claim 11, wherein the bottom housing structure includes a protrusion located horizontally opposite the integral toe portion and configured to contact and interlock with the base unit when the device is within the cavity.

19. The electronic device of claim 18, wherein:
the protrusion is integral with the bottom housing structure, located below the integral toe portion, and extends horizontally away from a peripheral surface thereof; and
further comprising:
one or more ultrasonic weld spots attaching the bottom housing structure to the top housing structure, wherein the one or more ultrasonic weld spots are located between the protrusion and the integral toe portion.

20. A method of manufacturing an electronic device, the method comprising:
providing a bottom housing structure;
providing a top housing structure including an integral toe;
aligning the top housing structure and the bottom housing structure along a plane, wherein the top housing structure overlaps the bottom housing or a portion therein and directly contacts the bottom housing at one or more locations; and
ultrasonically welding the bottom housing structure and the top housing structure by applying ultrasonic energy to the top housing structure, the bottom housing structure, a portion therein, or a combination thereof, wherein the integral toe is configured to provide a snap-fit for the ultrasonically welded combination of the bottom housing structure and the top housing structure when the ultrasonically welded combination is placed within a cavity of a base unit with the bottom housing structure facing the cavity and the top housing structure over the bottom housing structure.

* * * * *